US009591269B2

(12) United States Patent
Stevenson

(10) Patent No.: US 9,591,269 B2
(45) Date of Patent: *Mar. 7, 2017

(54) VIDEO INSPECTION METHOD FOR INSPECTING WELDS, STRUCTURAL BEAMS, AND UNDERDECKS OF MARINE VESSELS AND LIKE STRUCTURES

(71) Applicant: ULTRASONICS AND MAGNETICS CORPORATION, Harvey, LA (US)

(72) Inventor: Michael Stevenson, Slidell, LA (US)

(73) Assignee: ULTRASONICS AND MAGNETICS CORPORATION, Slidell, LA (US)

( * ) Notice: Subject to any disclaimer, the term of this patent is extended or adjusted under 35 U.S.C. 154(b) by 754 days.

This patent is subject to a terminal disclaimer.

(21) Appl. No.: 13/868,604

(22) Filed: Apr. 23, 2013

(65) Prior Publication Data
US 2013/0342679 A1    Dec. 26, 2013

Related U.S. Application Data

(63) Continuation of application No. 11/568,217, filed as application No. PCT/US2004/012480 on Apr. 21, (Continued)

(51) Int. Cl.
*H04N 7/18* (2006.01)
*G01N 21/88* (2006.01)

(52) U.S. Cl.
CPC .......... *H04N 7/18* (2013.01); *G01N 21/8803* (2013.01); *G01N 2021/889* (2013.01)

(58) Field of Classification Search
CPC ......... G01N 2021/889; G01N 21/8803; G01R 19/1658; H04N 7/18
See application file for complete search history.

(56) References Cited

U.S. PATENT DOCUMENTS 4,824,228 A * 4/1989 Wickholm ............. G02B 21/22
359/376
5,016,098 A * 5/1991 Cooper .............. A61B 1/00091
348/66
(Continued)

*Primary Examiner* — Nhon Diep
(74) *Attorney, Agent, or Firm* — Garvey, Smith, Nehrbass & North, L.L.C.; Charles C. Garvey, Jr.; Seth M. Nehrbass

(57) ABSTRACT

A method for inspecting a marine vessel underdeck utilizes a video camera such as a digital video camera with a magnifying or telephoto lens. The method produces a magnified image on a monitor for viewing by an inspector that appears to be no more than about 24 inches (61 cm) away. The method includes the step of filming the uuderdeck of a distance of about 40-70 feet (12-21 m). The lens provides a focal length of between about 15 feet (4.6 m) and 150 feet (46 m). Thus the method is conducted at a workable focal range of between about 15 feet (4.6 m) and 150 feet (46 m). The lens preferably has a focal length of between 30 feet (9 m) and 75 feet (23 m). The method includes the step of scanning the suspect area of the underdeck of a speed of about 1 inch (2.54 cm) per second to three feet (91.4 cm) per second. The preferred method contemplates scanning of the suspect area of a rate of between about 0.5-1 foot (15.2-30.5 cm) per second. The digital video can be focused on a particular area for about 15-30 seconds to create a loop for vetting.

20 Claims, 6 Drawing Sheets

Related U.S. Application Data 2004, now Pat. No. 8,441,531, which is a continuation-in-part of application No. 09/578,170, filed on May 24, 2000, now Pat. No. 6,741,274.

(60) Provisional application No. 60/135,478, filed on May 24, 1999.

(56) References Cited

U.S. PATENT DOCUMENTS

| | | | | |
|---|---|---|---|---|
| 5,115,307 A | * | 5/1992 | Cooper | A61B 1/00091 |
| | | | | 348/66 |
| 5,251,025 A | * | 10/1993 | Cooper | A61B 1/00091 |
| | | | | 348/66 |
| 5,420,632 A | * | 5/1995 | Yamagiwa | H04N 5/232 |
| | | | | 348/240.3 |
| 5,429,502 A | * | 7/1995 | Cooper | A61B 1/00091 |
| | | | | 348/66 |
| 5,479,203 A | * | 12/1995 | Kawai | H04N 5/232 |
| | | | | 348/14.1 |
| 5,515,206 A | * | 5/1996 | Peng | G02B 3/00 |
| | | | | 359/672 |
| 5,543,840 A | * | 8/1996 | Hirota | G02B 7/102 |
| | | | | 348/345 |
| 5,567,273 A | * | 10/1996 | Offerhaus | 162/198 |
| 5,568,735 A | * | 10/1996 | Newkirk | F25D 3/08 |
| | | | | 62/371 |
| 5,572,277 A | * | 11/1996 | Uzawa | G02B 15/173 |
| | | | | 359/686 |
| 5,808,810 A | * | 9/1998 | Mihara | G02B 15/173 |
| | | | | 359/684 |

\* cited by examiner

VIDEO INSPECTION METHOD FOR INSPECTING WELDS, STRUCTURAL BEAMS, AND UNDERDECKS OF MARINE VESSELS AND LIKE STRUCTURES

CROSS-REFERENCE TO RELATED APPLICATIONS

This is a continuation of my U.S. patent application Ser. No. 11/568,217, filed 8 Oct. 2007, published as U.S. Patent Publication No. 2008/0266390 on 30 Oct. 2008, which is a U.S. National Stage Entry of PCT/US04/12480, filed 21 Apr. 2004, which is a continuation-in-part of my U.S. patent application Ser. No. 09/578,170, filed 24 May 2000, issued as U.S. Pat. No. 6,741,274 on 25 May 2004, which claims priority from my U.S. Provisional Patent Application Ser. No. 60/135,478, filed 24 May 1999, all of which are hereby incorporated herein by reference.

Priority of my U.S. Provisional Patent Application Ser. No. 60/135,478, filed 24 May 1999, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to the inspection of marine vessels such as barges, bulk carriers, and tankers and particularly the underdeck structure including the beams, girders, welds, and stiffeners. Even more particularly, the present invention relates to an improved method of video inspection for barges, ships, and other marine vessels, that employs video imaging, preferably a digital video camera and a high resolution telephotomagnifying lens that scans an area (such as a suspect area) of a vessel, such as for example the underdeck area of a barge.

2. General Background of the Invention

The inspection of marine vessels such as barges and ships requires that an inspector be within about 24 inches (about 61 em) of the area to be inspected so that any cracks flaws, corrosion or pitting can be observed in welds, beams, girders, stringers and other structural members. This presents a problem for inspection of under deck areas of very large vessels because the underdeck area can be a long distance away from any floor or like supporting surface that could be occupied by an inspector.

To provide for inspection of under deck areas of barges, bulk carriers, and tankers, the owner is typically required "stage out" the cargo hold so that the surveyor or inspector can be placed very close to the structure being inspected. This can be a very expensive proposition costing hundreds of thousands of dollars for a very large vessel such as a four hundred foot (120 m) ship or a five hundred foot (150 m) barge.

Patents have issued that discuss video inspection using digital video cameras and a telephoto lens. The Offerhause et al. patent, U.S. Pat. No. 5,567,273, entitled "Method of Reducing Surface Irregularities in Paper Machine Head Box Components" discussed video inspection of hole inlet radii to provide further evidence of non-uniformities related to streak locations. A digital video camera inspection technique is discussed using CCD (Charged Coupled Device) technology to obtain distortion free images of superior quality and resolution. Halogen "broom" lighting is provided in order to give clear contrast and a telephoto lens to ensure a flat image. The images are then digitized for detailed computer analysis to an accuracy of 0.1 millimeters (0.004 inch), in a manner similar to using an optical comparator. This technique was said to be useful for inspection of the apron floor joint, turbulence generator perforated plate, and inlet tube bank Offerhause is not directed to long distance inspection of marine vessels.

The Mueller patent, U.S. Pat. No. 5,508,735, entitled "Underdeck Inspection Device"relates to an apparatus and method for the remote visualization and inspection of an internal storage space, such as a ship's hold. The apparatus includes a mounting stand to which is rotationally mounted a support shaft, the support shaft having a camera and a light source secured thereto. The camera and light source rotate with the support shaft, and are pivotally movable relative to the support shaft. A drive shaft extends through the support shaft and is operable to simultaneously pivot the light source camera. A light adjustment drive shaft is mounted to the hollow support shaft and allows the operator to pivot the light source independently of the camera to permit a wider field of view than would otherwise be available. The apparatus is inserted, via an exterior access opening, into a storage space and thereafter operated to allow an inspector, located outside of the storage space, to visually inspect the surfaces surrounding and defining the storage space. The Mueller device does not cover many areas (and is therefore unacceptable) because it rotates about a fixed center. It is only functional from the outside of the tank.

A stereo microscopic inspection system that employs a telephoto objective assembly is the subject of U.S. Pat. No. 4,824,228.

Electronic video dental cameras that employ telephoto lenses are disclosed in U.S. Pat. Nos. 5,016,098; 5,115,307; 5,251,025; and 5,429,502. Other patents that discuss the use of a telephoto lens with a video camera include U.S. Pat. Nos. 5,808,810; 5,572,277; 5,543,840; 5,515,206; 5,479,203; 5,420,632; 5,290,168; 5,285,317; and 15 5,260,834.

The following US patents were cited in a corresponding US patent application: Strait et al (U.S. Pat. No. 5,355,818), Chang et al (U.S. Pat. No. 4,750,035), Minami (U.S. Pat. No. 5,905,595), Jones (U.S. Pat. No. 6,301,371), McDonald (U.S. Pat. No. 6,401,983) and Levine (U.S. Pat. No. 3,780,224).

BRIEF SUMMARY OF THE INVENTION

The present invention provides an improved method for video inspection of the inside of a marine vessel, barge, ship, etc. The present invention provides an apparatus and a method for inspecting surfaces including those that are suspect such as welds, beams, underdeck surface, girders and the like. The present invention provides full coverage even into comers, and the coverage is overlapping.

For the method of the present invention, there is provided a video camera having a lens. The lens is preferably a telephoto lens and/or magnifying lens that provides a closeup view for an inspector that views a monitor or a video tape after inspection is completed. Preferably, the inspector views the monitor in real time while the inspection is occurring.

As part of the method, the underdeck for example of a barge is filmed from a distance of far away such as 15-75 feet (4.6-22.9 m) and preferably from a distance of 40-70 feet (12.2-21.4 m).

The lens has a focal length of between 5 feet (1.5 m) and infinity, preferably a focal length of between 15 feet (4.6 m) and 150 feet (45.8 m).

When the video image appears on a monitor, it is magnified and appears less than 24 inches (61 cm) away from the inspector. The inspector typically views an image that appears to be less than twelve inches (30.5 cm) away, and typically about one half inch—six inches (1.27-15.2 cm) away.

This method provides a high resolution close-up image that enables an inspector to view the video tape image and spot any cracks, pitting, corrosion, flaws, etc.

The preferred millimeter ranges of the lenses preferably used in the present invention are between about 75 mm-500 mm, more preferably between about 10 mm-400 mm, and most preferably between about 100 mm-300 mm.

The operator could be on the floor, or he could be elevated on scaffolding or on a ladder. When inspecting sides of tank, the operator is typically between about 5-30 m away from the side, and more typically between about 5-20 m.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
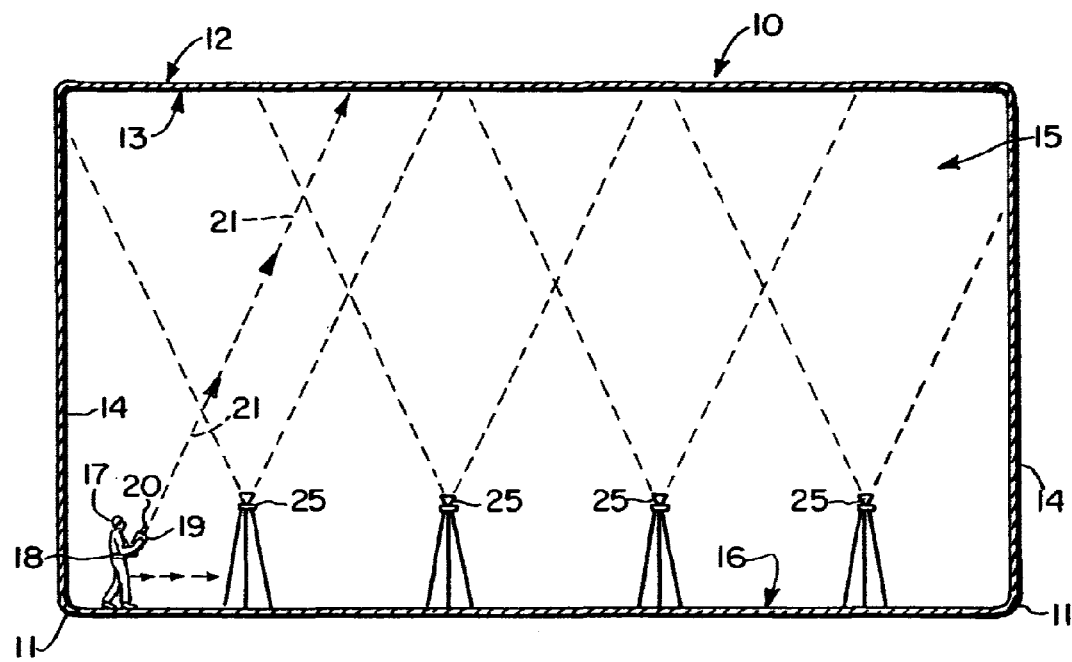
FIG. 1 is a schematic side elevational view showing the method and apparatus of the present invention.
Figure 2:
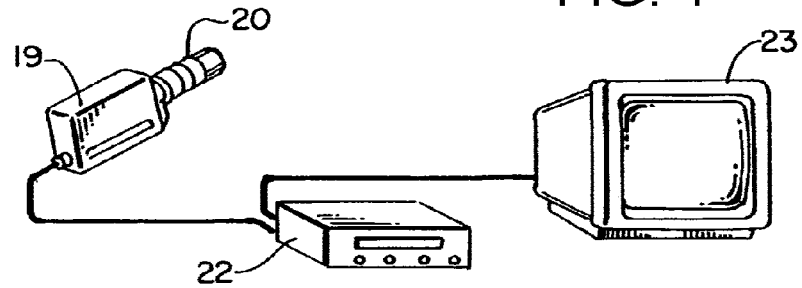
FIG. 2 is a schematic diagram showing the apparatus of the present invention.
Figure 3:
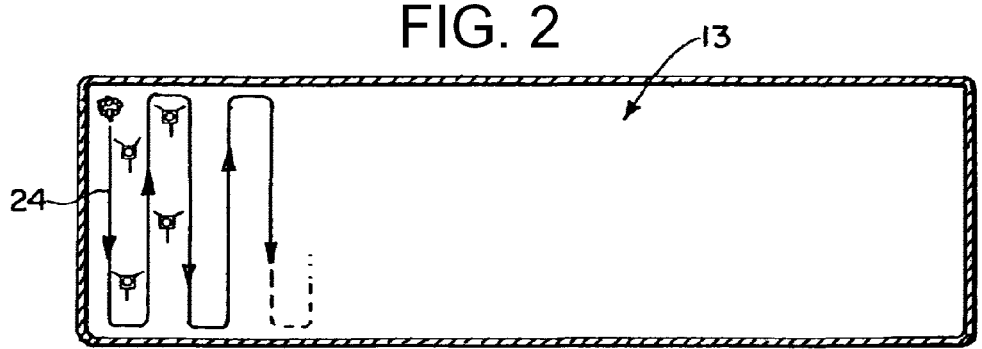
FIG. 3 is a plan view illustrating the method of the present invention.

FIG. 1 shows the apparatus of the present invention designated generally by the numeral 10. In FIGS. 1-3, inspection apparatus 10 is shown in use filming the underdeck area 13 of a marine vessel 11. Vessel 11 (e.g. a barge) has an interior hold 15 surrounded by deck, floor, and side walls. In FIG. 1, vessel 11 has a tank or hold 15 that is surrounded by deck 12, walls 14 and floor 16. An underdeck 13 is typically the area to be inspected for pitting, cracks, and other flaws. Underdeck 13 can include plate, structural members, welds, beams, and girders, for example.

The method of the present invention contemplates the inspection of structural members, welds, beams, girders and plates. In FIG. 1, an inspector 17 wears a harness 18 that supports digital camera 19. The harness is preferably a steadying type harness such as the commercially available Glidecam® 1000 Pro harness. In FIG. 2, a schematic diagram shows digital video camera 19 with a telephoto/magnifying lens 20. During inspection of the barge 11 underdeck 13, monitor 23 can be viewed in real time, or a recorder 22 can be used to record a video tape of the underdeck 13 for later close up visualization. Lighting units 25 can be employed to illuminate the underdeck 13 to remove any shadows. At the time of the inspection, monitor 23 can be connected to the camera 19 with recorder 22 for simultaneously recording and inspecting for cracks, pitting, flaws, etc. In such a case, both real time and subsequent inspection is enabled. Videotape or a film recorded (e.g. by recorder 22) and can preferably be later viewed and/or analyzed.

In FIG. 3, the barge underdeck 13 is shown schematically, wherein an inspection path 24 is mapped out as a preselected grid. For example, the image captured by the camera 19 and lens 20 focused along line sight 21 can be for example between about 6 inches (15.2 cm) and 2 feet (61 cm) in diameter. The inspection path 24 would preferably be an overlapping grid path so that the video images overlap six inches (15.2 cm), for example.

The method of the present invention thus provides a quick, simple yet workable solution to the problem of inspecting the underdeck of a barge or other remote surface to be inspected. With the present invention, there is no need for complicated scaffolding, robotic arm, or like equipment. The inspector 17 simply needs to obtain access to the hold 15 so that the areas can be filmed from a distance, preferably between about 15 feet (4.6 m) and 150 feet (46 m).

The present invention utilizes components that are commercially available such as a digital camera Canon, Nikon, or any digital camera available from Canadian Photonic Labs. The lenses can be telephoto lenses such as a 500 millimeter fixed aperture mirror lens manufactured by Canon, Nikon, or Samyang. The lenses can be modified to provide a focal length of between about 15 feet (4.6 m) and 150 feet (46 m), preferably between about 30 feet (9.2 m) and 75 feet (23 m).

Figure 4:
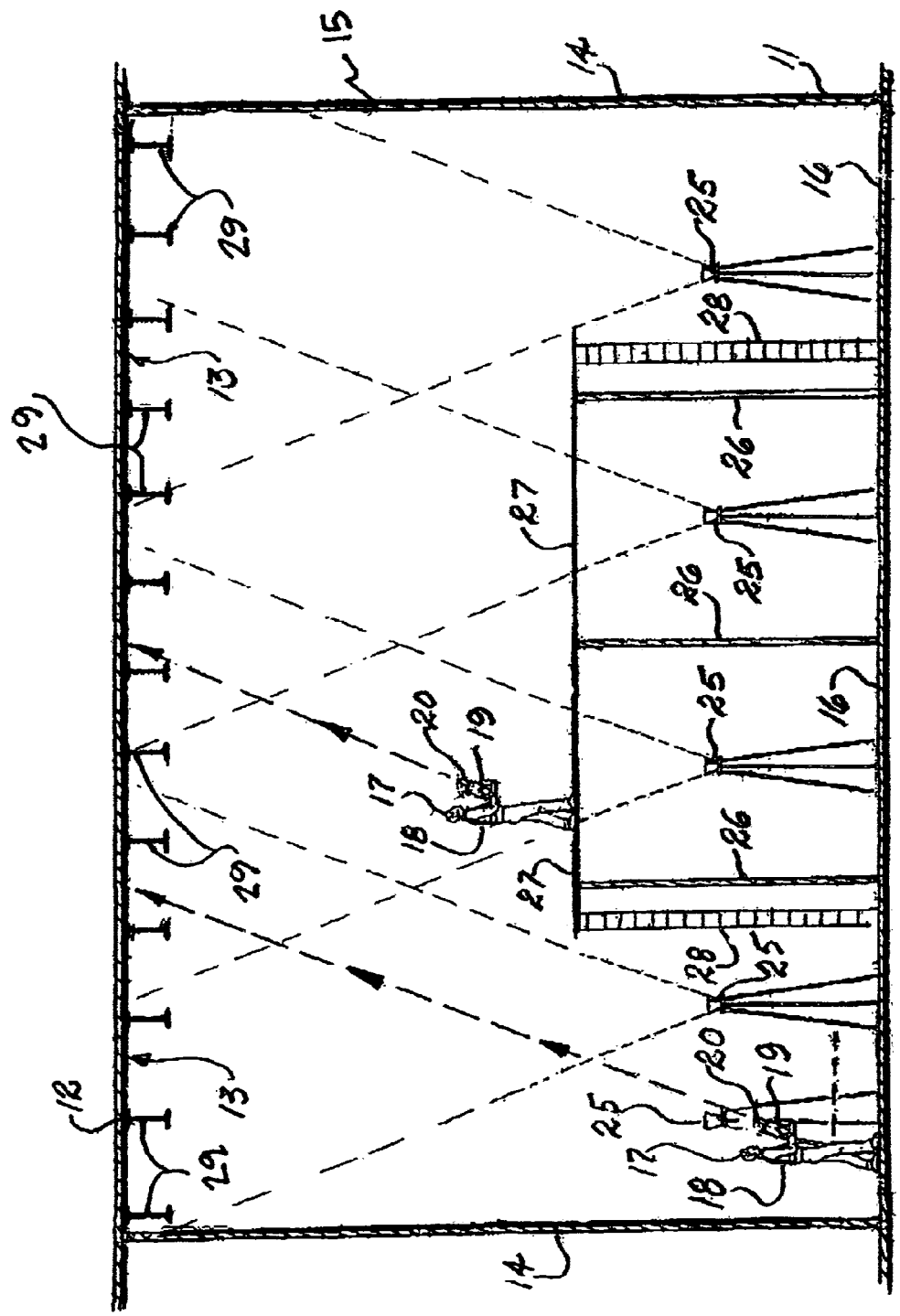
FIG. 4 is a schematic perspective diagram of an alternate method of the present invention.
Figure 5A:
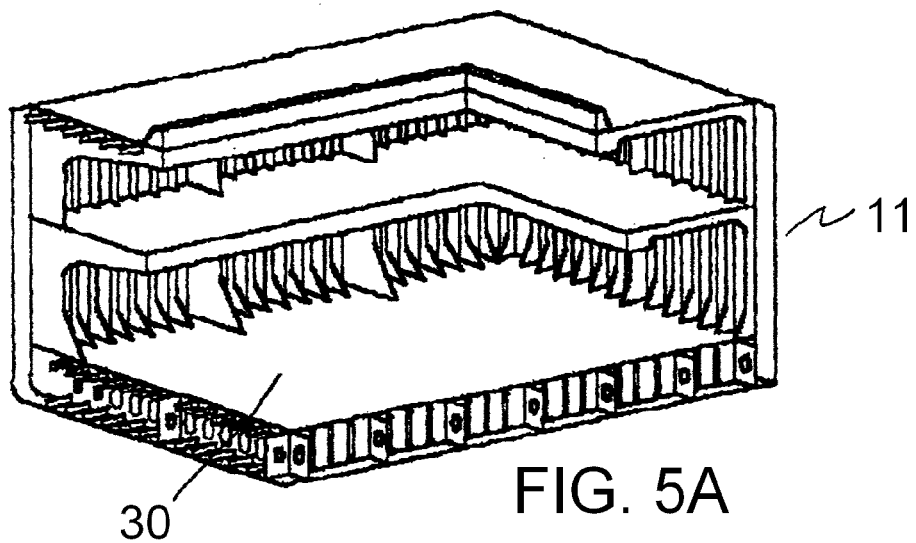
FIGS. 5A-5F are schematic perspective views of other hull underdeck configurations that can be inspected using the method and apparatus of the present invention.
Figure 5B:
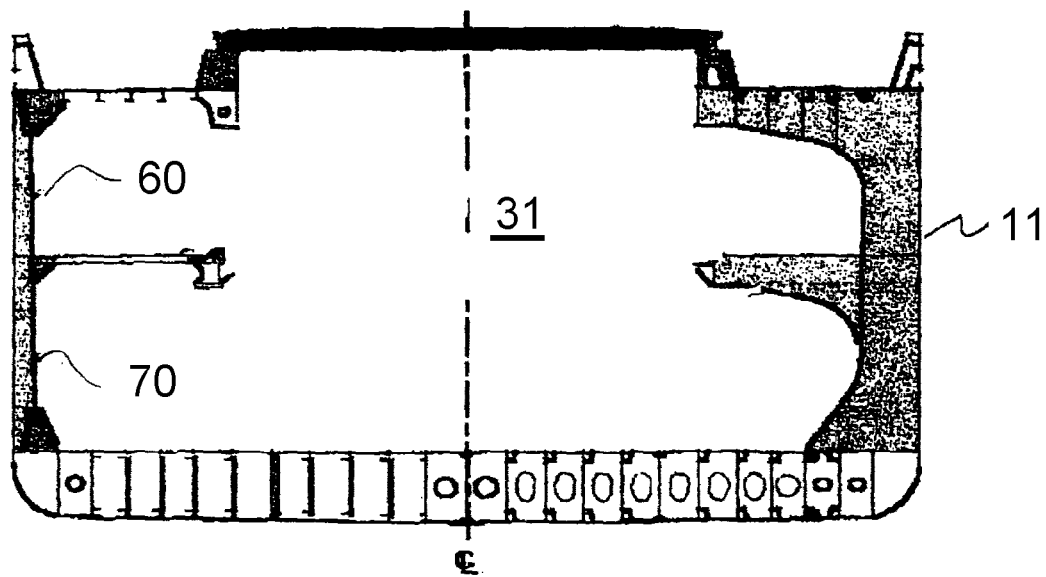
Figure 5C:
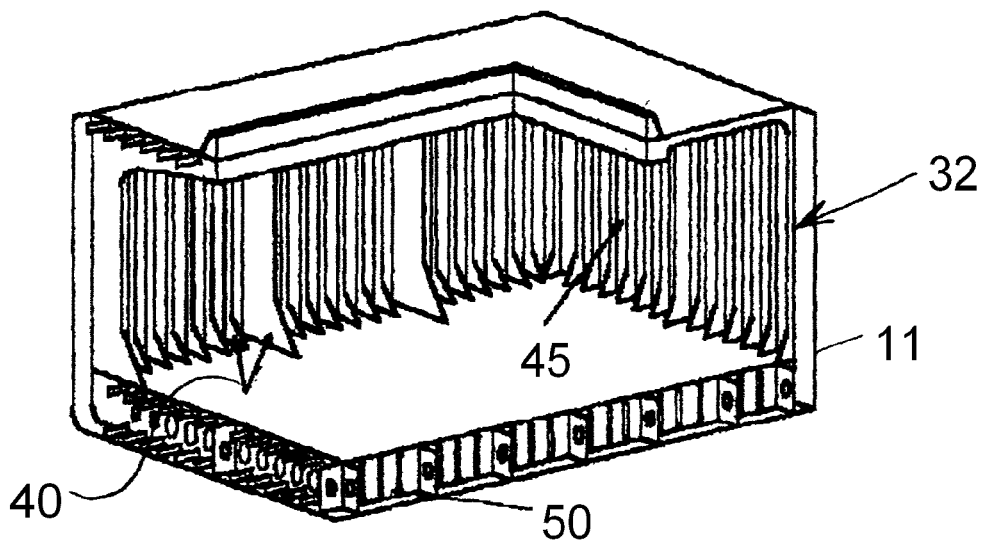
Figure 5D:
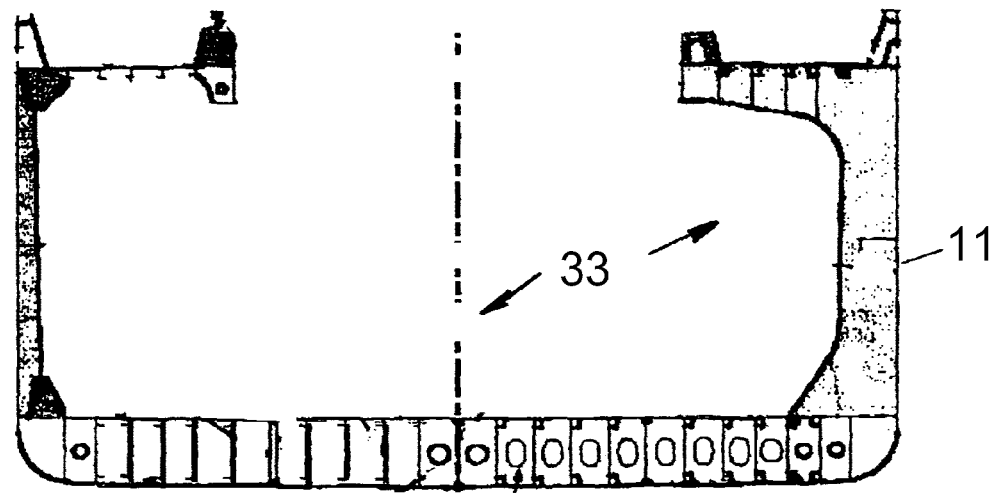
Figure 5E:
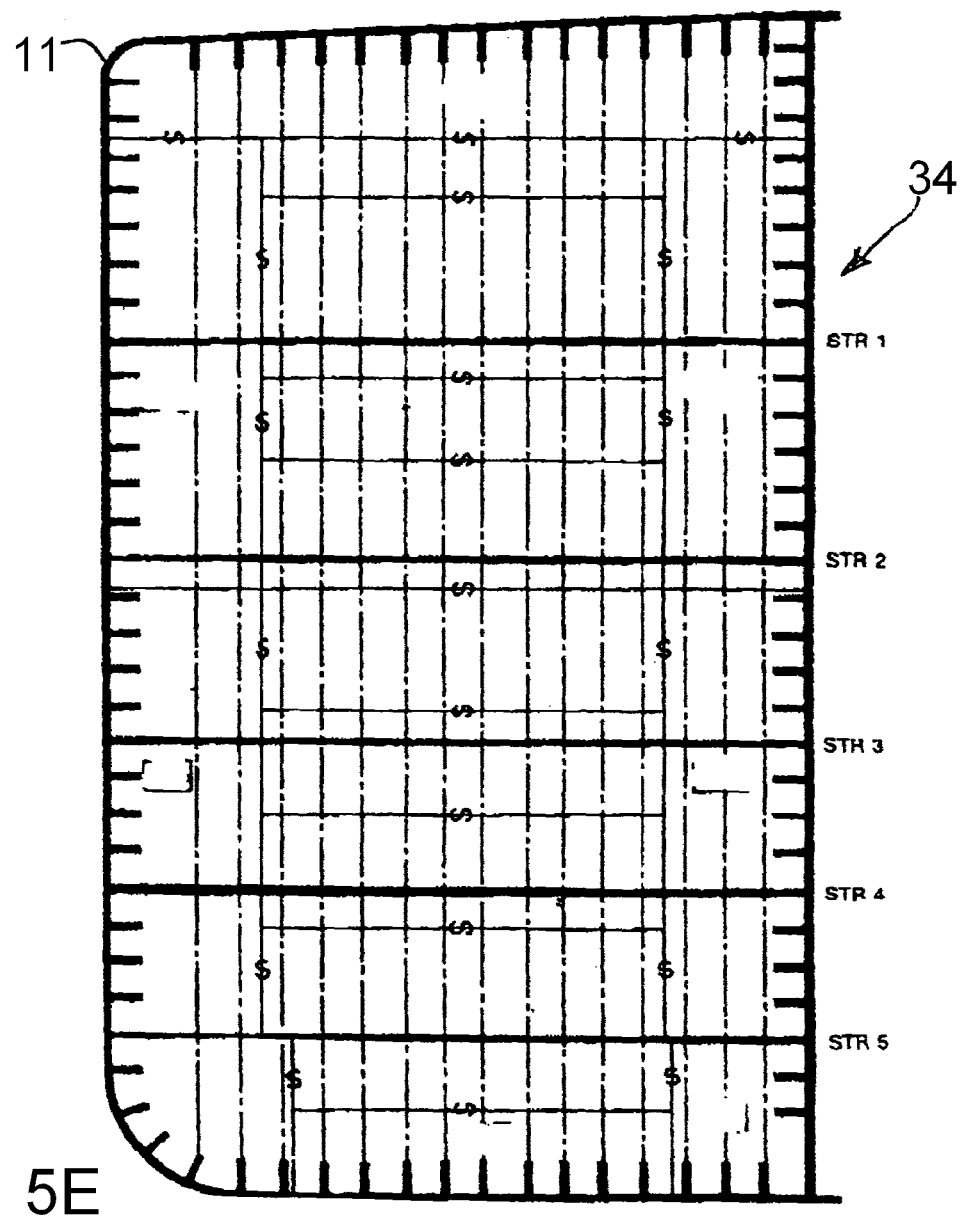
Figure 5F:
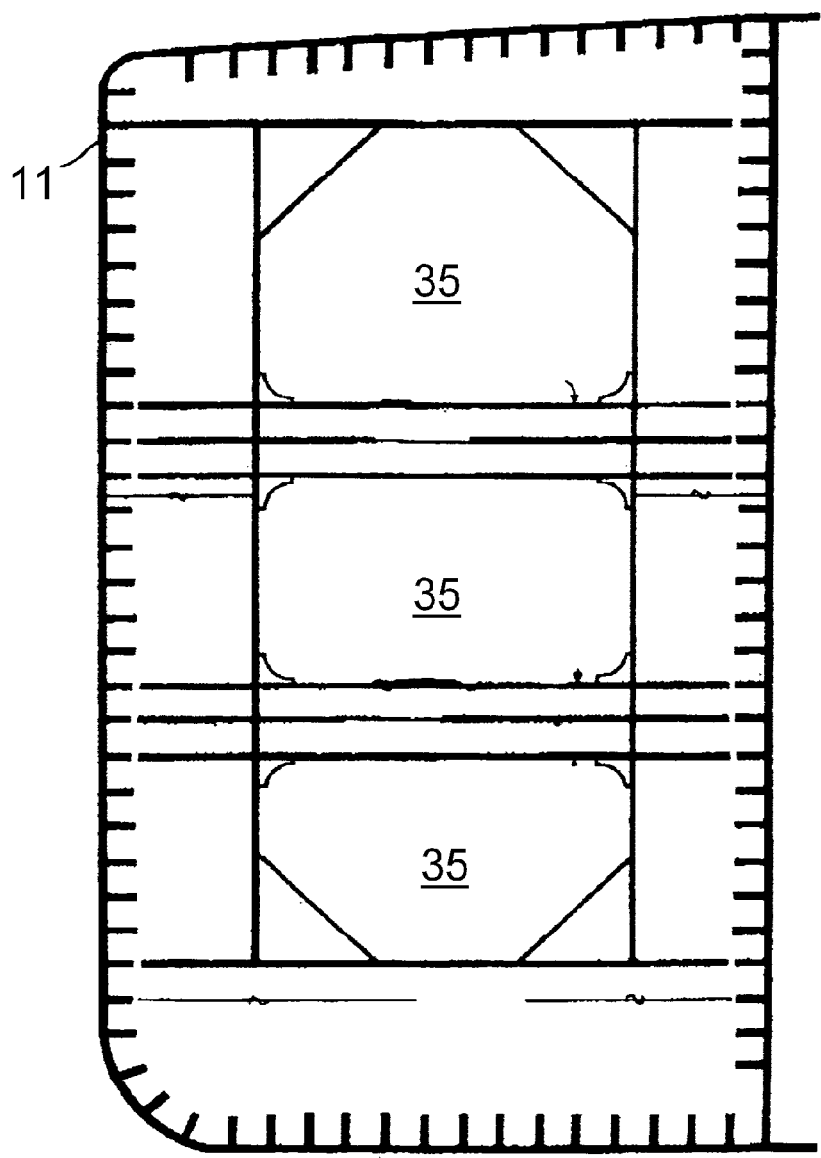

FIG. 4 illustrates the method and apparatus of the present invention wherein the hold 15 of a vessel 11 has obstructions on floor 16 (such as the baffles or partitions 26) and underdeck beams 29 next to underdeck 13 as shown. In such a situation, a platform can be placed above the baffles 26 so that the inspector 17 can conduct the inspection using camera 19 and lens 20 while walking on platform 27, following a predetermined inspection 15 path 24. The inspector 17 thus walks on floor 16 for part of the inspection and on platform 27 for part of the inspection. Ladders 28 provide access to platform 27. In FIG. 4, the inspector is typically spaced from the underdeck 13 a distance of typically between about 10 m and 15 m.

It should be understood that the method and apparatus of the present invention can be used to inspect cargo holds that have a different configuration than the ones shown in FIGS. 1, 3 and 4. For example, FIGS. 5A-5F show various other hull 11 constructions wherein each of the holds differs in construction from the other. FIGS. 5A-5E are examples of holds 30, 31, 32, 33, 34, 35 respectively that can be inspected using the method and apparatus of the present invention.

The present invention can be used to inspect welds, beams, plate, coating, etc. for pitting corrosion or flaws in underdeck areas of ships or other marine vessels.

The following table lists the parts numbers and parts descriptions as used herein and in the drawings attached hereto.

PARTS LIST

| Part Number | Description |
| --- | --- |
| 10 | inspection apparatus |
| 11 | marine vessel |
| 12 | deck |
| 13 | underdeck |
| 14 | wall |
| 15 | hold |
| 16 | floor |
| 17 | inspector |
| 18 | harness |
| 19 | digital video camera (preferably one that takes motion pictures) |
| 20 | telephoto lens |
| 21 | line of sight |
| 22 | recorder |
| 23 | monitor |
| 24 | inspection path |
| 25 | lighting unit |
| 26 | baffles |
| 27 | platform |
| 28 | ladder |
| 29 | underdeck beams |
| 30 | hold |
| 31 | hold |
| 32 | hold |
| 33 | hold |
| 34 | hold |
| 35 | hold |
| 40 | side shell frames and end brackets |
| 45 | transverse bulk head |
| 50 | double bottom tank |
| 60 | side shell frame (twin deck frame) |
| 70 | side shell frame (hold frame) |
| STR1 | stringer |
| STR2 | stringer |
| STR3 | stringer |
| STR4 | stringer |
| STR5 | stringer |

The video camera can be either digital (preferably) or analog. For example (and preferably), the video camera could record digitally on a video tape or other electronic digital media, such as DV, DVD, or CD.

As used herein, the term "film" can mean a motion picture recorded on a video tape or other electronic digital media, such as DV, DVD, or CD.

Though this invention has been described in conjunction with barges, the present invention can advantageously be used with other vessels.

The foregoing embodiments are presented by way of example only; the scope of the present invention is to be limited only by the following claims.

The invention claimed is:

1. A method of inspecting a vessel underdeck comprising the steps of:
   a) providing a camera with a lens;
   b) imaging the underdeck to generate a full coverage visual record that appears to be no more than 24 inches away from a viewer; and
   c) reviewing the visual record to inspect for defects.

2. The method of claim 1, further comprising the step of scanning the underdeck.

3. The method of claim 1, further comprising the step of scanning the underdeck at a speed of about 1 inch (2.54 cm) per second to about three feet (91.4 cm) per second.

4. The method of any of claim 1, further comprising the step of scanning the underdeck at a speed of about 1 foot (30.5 cm) per second.

5. The method of claim 1, further comprising filming the underdeck while following a selected grid path that includes a plurality of overlapping paths.

6. The method of claim 1, further comprising inspecting the underdeck while following a selected grid path that includes a plurality of overlapping paths.

7. The method of claim 1 wherein in step "d" the record is a videotape record.

8. A method of inspecting an underdeck surface of a vessel tank that has multiple surfaces including a floor surface, an underdeck surface, and side wall surfaces, comprising the steps of:
   a) providing a camera with a lens;
   b) positioning the camera in between the floor and the underdeck surface;
   c) generating a full coverage visual record that can be viewed by an inspector and appears to be no more than 24 inches away from the inspector; and
   d) reviewing the visual record to inspect for defects.

9. The method of claim 8, further comprising the step of scanning the underdeck surface.

10. The method of claim 8, further comprising the step of scanning the underdeck surface at a speed of about 1 inch (2.54 cm) per second to about three feet (91.4 cm) per second.

11. The method of claim 8, further comprising the step of scanning the underdeck surface at a speed of about 1 foot (30.5 cm) per second.

12. The method of claim 8, further comprising filming the underdeck surface while following a selected grid path that includes a plurality of overlapping paths.

13. The method of claim 8, further comprising inspecting the underdeck surface while following a selected grid path that includes a plurality of overlapping paths.

14. A method of inspecting a vessel underdeck of a vessel tank that includes a floor, side walls and a a vessel underdeck, comprising the steps of:
   a) providing a camera with a lens;
   b) imaging the vessel underdeck while following a selected grid path to generate a full coverage visual record that appears to be no more than 24 inches away from a viewer;
   c) positioning the camera in between the floor and vessel underdeck;
   d) wherein an inspector moves the camera to follow the selected grid path in step"b"; and
   e) reviewing the visual record to inspect for defects.

15. The method of claim 14 wherein in step "d" a videotape record is generated.

16. The method of claim 14 wherein in step "d" the visual record is displayed on a monitor.

17. The method of claim 14, further comprising the step of scanning the underdeck.

18. The method of claim 14, further comprising the step of scanning the underdeck at a speed of about 1 inch (2.54 cm) per second to about three feet (91.4 cm) per second.

19. The method of claim 14, further comprising the step of scanning the underdeck surface at a speed of about 1 foot (30.5 cm) per second.

20. The method of claim 14, further comprising filming the underdeck while following the selected grid path that includes a plurality of overlapping paths.

* * * * *